(12) United States Patent
Reglos et al.

(10) Patent No.: US 8,523,865 B2
(45) Date of Patent: Sep. 3, 2013

(54) TISSUE SPLITTER

(75) Inventors: Joey Camia Reglos, Lake Forest, CA (US); Moti Altarac, Irvine, CA (US)

(73) Assignee: Exactech, Inc., Gainesville, FL (US)

( * ) Notice: Subject to any disclaimer, the term of this patent is extended or adjusted under 35 U.S.C. 154(b) by 212 days.

(21) Appl. No.: 12/355,093

(22) Filed: Jan. 16, 2009

(65) Prior Publication Data
US 2009/0125047 A1    May 14, 2009

Related U.S. Application Data

(63) Continuation-in-part of application No. 11/586,849, filed on Oct. 25, 2006, which is a continuation-in-part of application No. 11/362,366, filed on Feb. 23, 2006.

(60) Provisional application No. 61/011,478, filed on Jan. 16, 2008, provisional application No. 60/701,660, filed on Jul. 22, 2005.

(51) Int. Cl.
*A61B 17/00*    (2006.01)

(52) U.S. Cl.
USPC ............... 606/79; 606/246; 606/83; 606/279; 606/170

(58) Field of Classification Search
USPC .................. 606/79, 82, 170, 246, 83, 279
See application file for complete search history.

(56) References Cited

U.S. PATENT DOCUMENTS

| 602,580 | A | | 4/1898 | Haskins et al. |
| 802,844 | A | | 10/1905 | Covell et al. |
| 2,790,437 | A | * | 4/1957 | Moore ........................ 600/564 |

(Continued)

FOREIGN PATENT DOCUMENTS

| EP | 0767636 | 4/1997 |
| EP | 0951246 | 10/1999 |

(Continued)

OTHER PUBLICATIONS

International Search Report and Written Opinion for application No. PCT/US09/031225, Mail Date Aug. 31, 2009, 14 pages.

(Continued)

*Primary Examiner* — Andrew Yang
*Assistant Examiner* — Olivia C Chang
(74) *Attorney, Agent, or Firm* — Meyertons, Hood, Kivlin, Kowert & Goetzel, P.C.; Eric B. Meyertons (57) ABSTRACT

A tissue splitter for creating a subcutaneous cut is disclosed. The tissue splitter includes a retractable blade located at the distal end. The tissue splitter is configured to be insertable into a slotted cannula that is placed via an incision to a location proximate a patient's spine. An actuator at the proximal end of the instrument projects the blade located at the distal end from its retracted state through the slot of the cannula to an extracted state to subcutaneously cut tissue at a location outside the cannula. The instrument is configured such that the blade is movable inside the slot of the cannula by a distance such that the cut created by the blade remains subcutaneous and does not puncture the skin of the patient. The distance is adjustable for the size and depth of the cut and is limited by an adjustment collar. The tissue splitter is ideally suited for creating a pathway for the subcutaneous insertion and implantation of a spinal stabilization rod between two bone anchors placed in vertebral bodies.

20 Claims, 7 Drawing Sheets

(56) References Cited

U.S. PATENT DOCUMENTS

| | | | |
|---|---|---|---|
| 4,545,374 A * | 10/1985 | Jacobson | 600/210 |
| 4,611,582 A | 9/1986 | Duff | |
| 4,743,260 A | 5/1988 | Burton | |
| 4,858,601 A | 8/1989 | Glisson | |
| 4,959,064 A | 9/1990 | Engelhardt | |
| 5,015,247 A | 5/1991 | Michelson | |
| 5,062,845 A | 11/1991 | Kuslich et al. | |
| 5,092,866 A | 3/1992 | Breard et al. | |
| 5,129,388 A | 7/1992 | Vianaud et al. | |
| 5,171,279 A | 12/1992 | Mathews | |
| 5,180,393 A | 1/1993 | Commarmond et al. | |
| 5,207,678 A | 5/1993 | Harms et al. | |
| 5,282,863 A | 2/1994 | Burton | |
| 5,368,594 A | 11/1994 | Martin et al. | |
| 5,370,646 A | 12/1994 | Reese et al. | |
| 5,375,823 A | 12/1994 | Navas et al. | |
| 5,387,212 A | 2/1995 | Yuan et al. | |
| 5,415,661 A | 5/1995 | Holmes | |
| 5,431,671 A * | 7/1995 | Nallakrishnan | 606/167 |
| 5,437,669 A | 8/1995 | Yuan et al. | |
| 5,437,672 A | 8/1995 | Alleyne | |
| 5,443,467 A | 8/1995 | Biedermann | |
| 5,449,355 A | 9/1995 | Rhum et al. | |
| 5,480,401 A | 1/1996 | Navas et al. | |
| 5,484,437 A | 1/1996 | Michelson | |
| 5,489,308 A | 2/1996 | Kuslich et al. | |
| 5,522,843 A | 6/1996 | Zang | |
| 5,527,312 A | 6/1996 | Ray | |
| 5,540,688 A | 7/1996 | Navas et al. | |
| 5,571,191 A | 11/1996 | Fitz | |
| 5,609,636 A | 3/1997 | Kohrs et al. | |
| 5,616,142 A | 4/1997 | Yuan et al. | |
| 5,645,599 A | 7/1997 | Samani et al. | |
| 5,658,337 A | 8/1997 | Kohrs et al. | |
| 5,672,175 A | 9/1997 | Martin | |
| 5,720,751 A | 2/1998 | Jackson | |
| 5,741,253 A | 4/1998 | Michelson | |
| 5,776,135 A | 7/1998 | Errico et al. | |
| 5,885,286 A | 3/1999 | Sherman et al. | |
| 5,891,145 A | 4/1999 | Morrison et al. | |
| RE36,211 E | 5/1999 | Nonomura | |
| 5,964,761 A | 10/1999 | Kambin | |
| 6,004,327 A | 12/1999 | Asnis et al. | |
| 6,014,588 A | 1/2000 | Fitz | |
| 6,033,406 A | 3/2000 | Mathews | |
| 6,063,088 A | 5/2000 | Winslow | |
| RE36,758 E | 6/2000 | Fitz | |
| 6,080,155 A | 6/2000 | Michelson | |
| 6,080,157 A | 6/2000 | Cathro et al. | |
| 6,096,038 A | 8/2000 | Michelson | |
| 6,132,464 A | 10/2000 | Martin | |
| 6,200,322 B1 | 3/2001 | Branch et al. | |
| 6,241,730 B1 | 6/2001 | Alby et al. | |
| 6,248,105 B1 | 6/2001 | Schlapfer et al. | |
| 6,261,293 B1 | 7/2001 | Nicholson et al. | |
| 6,264,656 B1 | 7/2001 | Michelson | |
| 6,267,764 B1 | 7/2001 | Elbera et al. | |
| 6,267,765 B1 | 7/2001 | Taylor et al. | |
| 6,270,498 B1 | 8/2001 | Michelson | |
| 6,287,764 B1 | 9/2001 | Hildebrand et al. | |
| 6,290,724 B1 | 9/2001 | Marino | |
| 6,304,140 B1 | 10/2001 | Thron et al. | |
| 6,306,140 B1 | 10/2001 | Siddiqui | |
| 6,348,053 B1 | 2/2002 | Cachia | |
| 6,375,657 B1 | 4/2002 | Doubler et al. | |
| 6,379,354 B1 | 4/2002 | Rogozinski et al. | |
| 6,419,703 B1 | 7/2002 | Fallin et al. | |
| 6,440,133 B1 | 8/2002 | Beale et al. | |
| 6,478,798 B1 | 11/2002 | Howland | |
| 6,485,491 B1 | 11/2002 | Farris et al. | |
| 6,485,518 B1 | 11/2002 | Cornwall et al. | |
| 6,530,929 B1 | 3/2003 | Justis et al. | |
| 6,533,790 B1 | 3/2003 | Liu | |
| 6,540,747 B1 | 4/2003 | Marino | |
| 6,547,795 B2 | 4/2003 | Schneiderman | |
| 6,554,830 B1 | 4/2003 | Chappius | |
| 6,558,390 B2 | 5/2003 | Cragg | |
| 6,562,046 B2 | 5/2003 | Sasso | |
| 6,565,565 B1 | 5/2003 | Yuan et al. | |
| 6,565,573 B1 | 5/2003 | Ferrante et al. | |
| 6,565,605 B2 | 5/2003 | Goble et al. | |
| 6,579,319 B2 | 6/2003 | Goble et al. | |
| 6,610,091 B1 | 8/2003 | Reiley | |
| 6,626,904 B1 | 9/2003 | Jammet et al. | |
| 6,626,905 B1 | 9/2003 | Schmiel et al. | |
| 6,626,944 B1 | 9/2003 | Taylor et al. | |
| 6,645,207 B2 | 11/2003 | Dixon et al. | |
| 6,645,248 B2 | 11/2003 | Casutt et al. | |
| 6,648,888 B1 | 11/2003 | Shluzas | |
| 6,660,006 B2 | 12/2003 | Markworth et al. | |
| 6,669,697 B1 | 12/2003 | Pisharodi | |
| 6,669,729 B2 | 12/2003 | Chin | |
| 6,676,661 B1 | 1/2004 | Martin Benlloch et al. | |
| 6,695,842 B2 | 2/2004 | Zucherman et al. | |
| 6,699,247 B2 | 3/2004 | Zucherman et al. | |
| 6,702,817 B2 | 3/2004 | Beger et al. | |
| 6,709,434 B1 | 3/2004 | Gournay et al. | |
| 6,716,214 B1 | 4/2004 | Jackson | |
| 6,716,245 B2 | 4/2004 | Pasquet et al. | |
| 6,726,687 B2 | 4/2004 | Jackson | |
| 6,726,689 B2 | 4/2004 | Jackson | |
| 6,730,089 B2 | 5/2004 | Jackson | |
| 6,740,086 B2 | 5/2004 | Richelsoph | |
| 6,740,090 B1 | 5/2004 | Cragg et al. | |
| 6,749,613 B1 | 6/2004 | Conchy et al. | |
| 6,749,614 B2 | 6/2004 | Teitelbaum et al. | |
| 6,761,720 B1 | 7/2004 | Seneqas et al. | |
| 6,770,075 B2 | 8/2004 | Howland | |
| 6,783,527 B2 | 8/2004 | Drewry et al. | |
| 6,786,903 B2 | 9/2004 | Lin | |
| 6,790,209 B2 | 9/2004 | Beale et al. | |
| 6,793,656 B1 | 9/2004 | Mathews | |
| 6,802,844 B2 | 10/2004 | Ferree | |
| 6,802,845 B2 | 10/2004 | Shirado et al. | |
| 6,805,697 B1 | 10/2004 | Helm et al. | |
| 6,811,567 B2 | 11/2004 | Reilev | |
| 6,821,277 B2 | 11/2004 | Teitelbaum | |
| 6,835,205 B2 | 12/2004 | Atkinson et al. | |
| 6,835,207 B2 | 12/2004 | Zacouto et al. | |
| 6,869,433 B2 | 3/2005 | Glascott | |
| 6,875,212 B2 | 4/2005 | Shaolian et al. | |
| 6,875,222 B2 * | 4/2005 | Long et al. | 606/172 |
| 6,884,244 B1 | 4/2005 | Jackson | |
| 6,896,677 B1 | 5/2005 | Lin | |
| 6,899,716 B2 | 5/2005 | Cragg | |
| 6,902,580 B2 | 6/2005 | Fallin et al. | |
| 6,949,123 B2 | 9/2005 | Reiley | |
| 6,966,910 B2 | 11/2005 | Ritland | |
| 6,966,930 B2 | 11/2005 | Arnin et al. | |
| 6,974,478 B2 | 12/2005 | Reilev et al. | |
| 6,989,011 B2 | 1/2006 | Paul et al. | |
| 6,997,927 B2 | 2/2006 | Jackson | |
| 7,008,422 B2 | 3/2006 | Foley et al. | |
| 7,011,660 B2 | 3/2006 | Sherman et al. | |
| 7,011,685 B2 | 3/2006 | Arnin et al. | |
| 7,029,475 B2 | 4/2006 | Paniabi | |
| 7,033,358 B2 | 4/2006 | Taylor et al. | |
| 7,041,136 B2 | 5/2006 | Goble et al. | |
| 7,051,451 B2 | 5/2006 | Auaostino et al. | |
| 7,052,497 B2 | 5/2006 | Sherman et al. | |
| 7,060,068 B2 | 6/2006 | Tromanhauser et al. | |
| 7,066,939 B2 | 6/2006 | Taylor | |
| 7,066,957 B2 | 6/2006 | Graf | |
| 7,070,598 B2 | 7/2006 | Lim et al. | |
| 7,074,237 B2 | 7/2006 | Goble et al. | |
| 7,074,238 B2 | 7/2006 | Stinson et al. | |
| 7,079,883 B2 | 7/2006 | Marino et al. | |
| 7,081,117 B2 | 7/2006 | Bono et al. | |
| 7,083,621 B2 | 8/2006 | Shaolian et al. | |
| 7,083,622 B2 | 8/2006 | Simonson | |
| 7,083,649 B2 | 8/2006 | Zucherman et al. | |
| 7,087,055 B2 | 8/2006 | Lim et al. | |
| 7,087,057 B2 | 8/2006 | Konieczynski et al. | |
| 7,087,084 B2 | 8/2006 | Reiley | |

| Patent/Pub No. | Date | Name |
|---|---|---|
| 7,090,698 B2 | 8/2006 | Goble et al. |
| 7,101,398 B2 | 9/2006 | Dooris et al. |
| 7,108,705 B2 | 9/2006 | Davison et al. |
| 7,125,410 B2 | 10/2006 | Freudiger et al. |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,156,849 B2 | 1/2007 | Dunbar et al. |
| 7,160,300 B2 | 1/2007 | Jackson |
| 7,182,783 B2 | 2/2007 | Trieu |
| 7,188,626 B2 | 3/2007 | Foley et al. |
| 7,204,853 B2 | 4/2007 | Gordon et al. |
| 7,207,992 B2 | 4/2007 | Ritland |
| 7,214,227 B2 | 5/2007 | Colleran et al. |
| 7,220,262 B1 | 5/2007 | Hynes |
| 7,229,441 B2 | 6/2007 | Trieu et al. |
| 7,250,052 B2 | 7/2007 | Landry et al. |
| 7,261,688 B2 | 8/2007 | Smith et al. |
| 7,278,995 B2 | 10/2007 | Nichols et al. |
| 7,282,065 B2 | 10/2007 | Kirschman |
| 7,291,150 B2 | 11/2007 | Graf et al. |
| 7,291,153 B2 | 11/2007 | Glascott |
| 7,294,129 B2 | 11/2007 | Hawkins et al. |
| 7,306,603 B2 | 12/2007 | Boehm, Jr. et al. |
| 7,329,258 B2 | 2/2008 | Studer et al. |
| 7,335,200 B2 | 2/2008 | Carli et al. |
| 7,354,453 B2 | 4/2008 | McAfee |
| 7,361,196 B2 | 4/2008 | Fallin et al. |
| 7,371,238 B2 | 5/2008 | Soboleski et al. |
| 7,377,921 B2 | 5/2008 | Studer et al. |
| 7,377,942 B2 | 5/2008 | Berry |
| 7,406,775 B2 | 8/2008 | Funk et al. |
| 7,445,635 B2 | 11/2008 | Fallin et al. |
| 7,465,306 B2 | 12/2008 | Pond, Jr. et al. |
| 7,470,279 B2 | 12/2008 | Jackson |
| 7,476,238 B2 | 1/2009 | Panjabi |
| 7,491,218 B2 | 2/2009 | Landry et al. |
| 7,493,019 B2 | 2/2009 | Moon et al. |
| 7,503,918 B2 | 3/2009 | Baccelli et al. |
| 7,527,638 B2 | 5/2009 | Anderson et al. |
| 7,547,318 B2 | 6/2009 | Birkmeyer et al. |
| 7,563,264 B2 | 7/2009 | Landry et al. |
| 7,569,061 B2 | 8/2009 | Colleran |
| 7,588,575 B2 | 9/2009 | Colleran et al. |
| 7,588,588 B2 | 9/2009 | Spitler et al. |
| 7,591,839 B2 | 9/2009 | Biedermann et al. |
| 7,615,068 B2 | 11/2009 | Timm et al. |
| 7,618,442 B2 | 11/2009 | Spitler et al. |
| 7,618,444 B2 | 11/2009 | Shluzas |
| 7,635,379 B2 | 12/2009 | Callahan et al. |
| 7,662,172 B2 | 2/2010 | Warnick |
| 7,678,137 B2 | 3/2010 | Butler et al. |
| 7,699,875 B2 | 4/2010 | Timm |
| 7,713,287 B2 | 5/2010 | Timm et al. |
| 7,713,288 B2 | 5/2010 | Timm et al. |
| 7,758,617 B2 | 7/2010 | Iott et al. |
| 7,935,134 B2 | 5/2011 | Reqlos et al. |
| 8,025,680 B2 | 9/2011 | Hayes et al. |
| 8,096,996 B2 | 1/2012 | Gutierrez et al. |
| 8,226,690 B2 | 7/2012 | Altarac et al. |
| 8,267,969 B2 | 9/2012 | Altarac et al. |
| 2001/0037111 A1 | 11/2001 | Dixon et al. |
| 2002/0026193 A1 | 2/2002 | Barker et al. |
| 2002/0032443 A1 | 3/2002 | Sherman et al. |
| 2002/0065557 A1 | 5/2002 | Goble et al. |
| 2002/0068975 A1 | 6/2002 | Teitelbaum et al. |
| 2002/0072800 A1 | 6/2002 | Goble et al. |
| 2002/0082599 A1 | 6/2002 | Crandall et al. |
| 2002/0082600 A1 | 6/2002 | Shaolian et al. |
| 2002/0091390 A1 | 7/2002 | Michelson |
| 2002/0095154 A1 | 7/2002 | Atkinson |
| 2002/0123806 A1 | 9/2002 | Reiley |
| 2002/0133154 A1 | 9/2002 | Saint Martin |
| 2002/0133155 A1 | 9/2002 | Ferree |
| 2002/0151895 A1 | 10/2002 | Soboleski et al. |
| 2002/0161368 A1 | 10/2002 | Foley et al. |
| 2002/0161370 A1 | 10/2002 | Frigg et al. |
| 2002/0173971 A1 | 11/2002 | Stirpe et al. |
| 2002/0183748 A1 | 12/2002 | Martin et al. |
| 2002/0198526 A1 | 12/2002 | Shaolian et al. |
| 2003/0004511 A1 | 1/2003 | Ferree |
| 2003/0004512 A1 | 1/2003 | Farris et al. |
| 2003/0004572 A1 | 1/2003 | Goble et al. |
| 2003/0018350 A1 | 1/2003 | Zucherman et al. |
| 2003/0023240 A1 | 1/2003 | Amrein et al. |
| 2003/0028250 A1 | 2/2003 | Reiley et al. |
| 2003/0032957 A1 | 2/2003 | McKinley |
| 2003/0032965 A1 | 2/2003 | Schneiderman |
| 2003/0040797 A1 | 2/2003 | Fallin et al. |
| 2003/0045878 A1 | 3/2003 | Petit et al. |
| 2003/0055426 A1 | 3/2003 | Carbone et al. |
| 2003/0055427 A1 | 3/2003 | Graf |
| 2003/0073996 A1 | 4/2003 | Doubler et al. |
| 2003/0073997 A1 | 4/2003 | Doubler et al. |
| 2003/0073998 A1 | 4/2003 | Pagliuca et al. |
| 2003/0125741 A1 | 7/2003 | Biedermann et al. |
| 2003/0149431 A1 | 8/2003 | Varieur |
| 2003/0153912 A1 | 8/2003 | Graf |
| 2003/0163133 A1 | 8/2003 | Altarac et al. |
| 2003/0171749 A1 | 9/2003 | Le Couedic et al. |
| 2003/0171750 A1 | 9/2003 | Chin |
| 2003/0191470 A1 | 10/2003 | Ritland |
| 2003/0199872 A1 | 10/2003 | Markworth et al. |
| 2003/0208202 A1 | 11/2003 | Falahee |
| 2003/0208203 A1 | 11/2003 | Lim et al. |
| 2003/0216735 A1 | 11/2003 | Altarac et al. |
| 2003/0220643 A1 | 11/2003 | Ferree |
| 2003/0229347 A1 | 12/2003 | Sherman et al. |
| 2004/0002708 A1 | 1/2004 | Ritland |
| 2004/0006341 A1 | 1/2004 | Shaolian et al. |
| 2004/0006344 A1 | 1/2004 | Nguyen et al. |
| 2004/0006391 A1 | 1/2004 | Reiley |
| 2004/0039384 A1 | 2/2004 | Boehm |
| 2004/0049189 A1 | 3/2004 | Le Couedic et al. |
| 2004/0049281 A1 | 3/2004 | Reiley |
| 2004/0064140 A1 | 4/2004 | Taylor et al. |
| 2004/0080418 A1 | 4/2004 | Dahlborn et al. |
| 2004/0082954 A1 | 4/2004 | Teitelbaum et al. |
| 2004/0087947 A1 | 5/2004 | Lim et al. |
| 2004/0092931 A1 | 5/2004 | Taylor et al. |
| 2004/0097933 A1 | 5/2004 | Lourdel et al. |
| 2004/0116927 A1 | 6/2004 | Graf |
| 2004/0127989 A1 | 7/2004 | Dooris et al. |
| 2004/0133208 A1 | 7/2004 | Weikel et al. |
| 2004/0138662 A1 | 7/2004 | Landry et al. |
| 2004/0143265 A1 | 7/2004 | Landry et al. |
| 2004/0143270 A1 | 7/2004 | Zucherman et al. |
| 2004/0147928 A1 | 7/2004 | Landry et al. |
| 2004/0147936 A1 | 7/2004 | Rosenberg et al. |
| 2004/0147937 A1 | 7/2004 | Dunbar, Jr. et al. |
| 2004/0215190 A1 | 10/2004 | Nguyen et al. |
| 2004/0225289 A1 | 11/2004 | Biedermann et al. |
| 2004/0230201 A1 | 11/2004 | Yuan et al. |
| 2004/0230304 A1 | 11/2004 | Yuan et al. |
| 2004/0236328 A1 | 11/2004 | Paul et al. |
| 2004/0236329 A1 | 11/2004 | Panjabi |
| 2004/0243126 A1 | 12/2004 | Carbone et al. |
| 2004/0249378 A1 | 12/2004 | Saint Martin et al. |
| 2004/0249380 A1 | 12/2004 | Glascott |
| 2004/0267260 A1 | 12/2004 | Mack et al. |
| 2005/0010217 A1 | 1/2005 | Dalton |
| 2005/0010953 A1 | 1/2005 | Carney et al. |
| 2005/0010954 A1 | 1/2005 | Binder |
| 2005/0010956 A1 | 1/2005 | Moon et al. |
| 2005/0021031 A1 | 1/2005 | Foley et al. |
| 2005/0027361 A1 | 2/2005 | Reiley |
| 2005/0033295 A1 | 2/2005 | Wisnewski |
| 2005/0033434 A1 | 2/2005 | Berry |
| 2005/0033436 A1 | 2/2005 | Schlapfer et al. |
| 2005/0033439 A1 | 2/2005 | Gordon et al. |
| 2005/0038429 A1 | 2/2005 | Elsebaie |
| 2005/0038430 A1 | 2/2005 | McKinley |
| 2005/0038432 A1 | 2/2005 | Shaolian et al. |
| 2005/0038440 A1 | 2/2005 | Larson et al. |
| 2005/0043742 A1 | 2/2005 | Bruneau et al. |
| 2005/0043797 A1 | 2/2005 | Lee |
| 2005/0043799 A1 | 2/2005 | Reiley |

| | | |
|---|---|---|
| 2005/0049588 A1 | 3/2005 | Jackson |
| 2005/0049589 A1 | 3/2005 | Jackson |
| 2005/0049705 A1 | 3/2005 | Hale et al. |
| 2005/0049708 A1 | 3/2005 | Atkinson et al. |
| 2005/0055031 A1 | 3/2005 | Lim |
| 2005/0055096 A1 | 3/2005 | Serhan et al. |
| 2005/0065515 A1 | 3/2005 | Jahng |
| 2005/0065516 A1 | 3/2005 | Jahng |
| 2005/0065517 A1 | 3/2005 | Chin |
| 2005/0070917 A1 | 3/2005 | Justis |
| 2005/0080418 A1 | 4/2005 | Simonson et al. |
| 2005/0080486 A1 | 4/2005 | Fallin et al. |
| 2005/0085813 A1 | 4/2005 | Spitler et al. |
| 2005/0085815 A1 | 4/2005 | Harms et al. |
| 2005/0101953 A1 | 5/2005 | Simonson |
| 2005/0101954 A1 | 5/2005 | Simonson |
| 2005/0101956 A1 | 5/2005 | Simonson |
| 2005/0113832 A1 | 5/2005 | Molz, IV et al. |
| 2005/0113927 A1 | 5/2005 | Malek |
| 2005/0119748 A1 | 6/2005 | Reiley et al. |
| 2005/0124991 A1 | 6/2005 | Jahng |
| 2005/0125066 A1 | 6/2005 | McAfee |
| 2005/0131405 A1 | 6/2005 | Molz et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131409 A1 | 6/2005 | Chervitz et al. |
| 2005/0131422 A1 | 6/2005 | Anderson et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137602 A1 | 6/2005 | Assell et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154461 A1 | 7/2005 | Humphreys et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0165396 A1 | 7/2005 | Fortin et al. |
| 2005/0171543 A1 | 8/2005 | Timm et al. |
| 2005/0171608 A1 | 8/2005 | Peterman et al. |
| 2005/0171609 A1 | 8/2005 | Humphrevs et al. |
| 2005/0171610 A1 | 8/2005 | Humphreys et al. |
| 2005/0177156 A1 | 8/2005 | Timm et al. |
| 2005/0177157 A1 | 8/2005 | Jahnq |
| 2005/0177164 A1 | 8/2005 | Walters et al. |
| 2005/0177166 A1 | 8/2005 | Timm et al. |
| 2005/0177240 A1 | 8/2005 | Blain |
| 2005/0182400 A1 | 8/2005 | White |
| 2005/0182401 A1 | 8/2005 | Timm et al. |
| 2005/0182409 A1 | 8/2005 | Callahan et al. |
| 2005/0187548 A1 | 8/2005 | Butler |
| 2005/0192570 A1 | 9/2005 | Jackson |
| 2005/0192574 A1 | 9/2005 | Blain |
| 2005/0192587 A1 | 9/2005 | Lim |
| 2005/0197700 A1 | 9/2005 | Boehm et al. |
| 2005/0197705 A1 | 9/2005 | Arnin et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0209593 A1 | 9/2005 | Kolb |
| 2005/0209694 A1 | 9/2005 | Loeb |
| 2005/0215999 A1* | 9/2005 | Birkmeyer et al. ............ 606/61 |
| 2005/0216000 A1 | 9/2005 | Colleran et al. |
| 2005/0222569 A1 | 10/2005 | Paniabi |
| 2005/0228378 A1 | 10/2005 | Kalfas et al. |
| 2005/0228381 A1 | 10/2005 | Kirschman |
| 2005/0234551 A1 | 10/2005 | Fallin et al. |
| 2005/0235508 A1 | 10/2005 | Augostino et al. |
| 2005/0240264 A1 | 10/2005 | Tokish et al. |
| 2005/0240265 A1 | 10/2005 | Kuioer et al. |
| 2005/0245928 A1 | 11/2005 | Colleran et al. |
| 2005/0245930 A1 | 11/2005 | Timm et al. |
| 2005/0249697 A1 | 11/2005 | Uhrich et al. |
| 2005/0261682 A1 | 11/2005 | Ferree |
| 2005/0261768 A1 | 11/2005 | Trieu |
| 2005/0273167 A1 | 12/2005 | Triolett et al. |
| 2005/0277921 A1 | 12/2005 | Eisermann et al. |
| 2005/0277922 A1 | 12/2005 | Trieu et al. |
| 2005/0288670 A1 | 12/2005 | Paniabi et al. |
| 2006/0004449 A1 | 1/2006 | Goble et al. |
| 2006/0004451 A1 | 1/2006 | Goble et al. |
| 2006/0015100 A1 | 1/2006 | Paniabi et al. |
| 2006/0025769 A1 | 2/2006 | Dick et al. |
| 2006/0036240 A1 | 2/2006 | Colleran et al. |
| 2006/0036244 A1 | 2/2006 | Soitler et al. |
| 2006/0036255 A1 | 2/2006 | Pond, Jr. et al. |
| 2006/0036260 A1 | 2/2006 | Runco et al. |
| 2006/0052785 A1 | 3/2006 | Auaostino et al. |
| 2006/0058791 A1 | 3/2006 | Broman et al. |
| 2006/0069391 A1 | 3/2006 | Jackson |
| 2006/0079894 A1 | 4/2006 | Colleran et al. |
| 2006/0079909 A1 | 4/2006 | Runco et al. |
| 2006/0084976 A1 | 4/2006 | Borastrom et al. |
| 2006/0084982 A1 | 4/2006 | Kim |
| 2006/0084984 A1 | 4/2006 | Kim |
| 2006/0084987 A1 | 4/2006 | Kim |
| 2006/0084991 A1 | 4/2006 | Borastrom et al. |
| 2006/0085072 A1 | 4/2006 | Funk et al. |
| 2006/0106380 A1 | 5/2006 | Colleran |
| 2006/0106394 A1 | 5/2006 | Colleran |
| 2006/0111713 A1 | 5/2006 | Jackson |
| 2006/0142759 A1 | 6/2006 | Arnin et al. |
| 2006/0142761 A1 | 6/2006 | Landry et al. |
| 2006/0149238 A1 | 7/2006 | Sherman et al. |
| 2006/0149239 A1 | 7/2006 | Winslow et al. |
| 2006/0149254 A1 | 7/2006 | Laurvssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0149375 A1 | 7/2006 | Yuan et al. |
| 2006/0149383 A1 | 7/2006 | Arnin et al. |
| 2006/0173454 A1 | 8/2006 | Spitler et al. |
| 2006/0189983 A1 | 8/2006 | Fallin et al. |
| 2006/0189984 A1 | 8/2006 | Fallin et al. |
| 2006/0190083 A1 | 8/2006 | Arnin et al. |
| 2006/0195086 A1 | 8/2006 | Sybert |
| 2006/0200137 A1 | 9/2006 | Soboleski et al. |
| 2006/0217718 A1 | 9/2006 | Chervitz et al. |
| 2006/0217719 A1 | 9/2006 | Albert et al. |
| 2006/0229616 A1 | 10/2006 | Albert et al. |
| 2006/0235388 A1 | 10/2006 | Justis et al. |
| 2006/0235393 A1 | 10/2006 | Bono et al. |
| 2006/0235414 A1 | 10/2006 | Lim et al. |
| 2006/0241593 A1 | 10/2006 | Sherman et al. |
| 2006/0241595 A1 | 10/2006 | Molz et al. |
| 2006/0241597 A1 | 10/2006 | Mitchell et al. |
| 2006/0241599 A1 | 10/2006 | Konieczynski et al. |
| 2006/0241642 A1 | 10/2006 | Amin et al. |
| 2006/0241758 A1 | 10/2006 | Peterman et al. |
| 2006/0241759 A1 | 10/2006 | Trieu |
| 2006/0241768 A1 | 10/2006 | Trieu |
| 2006/0241769 A1 | 10/2006 | Gordon et al. |
| 2006/0247623 A1 | 11/2006 | Anderson et al. |
| 2006/0247628 A1 | 11/2006 | Rawlins et al. |
| 2006/0247630 A1 | 11/2006 | Ion et al. |
| 2006/0247632 A1 | 11/2006 | Winslow et al. |
| 2006/0247633 A1 | 11/2006 | Winslow et al. |
| 2006/0247637 A1 | 11/2006 | Colleran et al. |
| 2006/0247649 A1 | 11/2006 | Rezach et al. |
| 2006/0247650 A1 | 11/2006 | Yerby et al. |
| 2006/0247658 A1 | 11/2006 | Pond, Jr. et al. |
| 2006/0247769 A1 | 11/2006 | Molz et al. |
| 2006/0247773 A1 | 11/2006 | Stamp |
| 2006/0260483 A1 | 11/2006 | Hartmann et al. |
| 2006/0264934 A1 | 11/2006 | Fallin |
| 2006/0264962 A1 | 11/2006 | Chin et al. |
| 2006/0265069 A1 | 11/2006 | Goble et al. |
| 2006/0271198 A1 | 11/2006 | McAfee |
| 2006/0276798 A1 | 12/2006 | Lim |

| | | |
|---|---|---|
| 2006/0276801 A1 | 12/2006 | Yerby et al. |
| 2006/0276897 A1 | 12/2006 | Winslow et al. |
| 2006/0282075 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert et al. |
| 2006/0293657 A1 | 12/2006 | Hartmann |
| 2006/0293690 A1 | 12/2006 | Abdelgany |
| 2006/0293692 A1 | 12/2006 | Whipple et al. |
| 2007/0005062 A1 | 1/2007 | Lange et al. |
| 2007/0005063 A1 | 1/2007 | Bruneau et al. |
| 2007/0016191 A1 | 1/2007 | Culbert et al. |
| 2007/0016193 A1 | 1/2007 | Ritland |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0016296 A1 | 1/2007 | Triplett et al. |
| 2007/0043358 A1 | 2/2007 | Molz, IV et al. |
| 2007/0043359 A1 | 2/2007 | Altarac et al. |
| 2007/0049931 A1 | 3/2007 | Justis et al. |
| 2007/0055242 A1 | 3/2007 | Bailly |
| 2007/0055257 A1 | 3/2007 | Vaccaro et al. |
| 2007/0073289 A1 | 3/2007 | Kwak et al. |
| 2007/0073396 A1 | 3/2007 | Arnin |
| 2007/0083264 A1 | 4/2007 | Arnin et al. |
| 2007/0090238 A1 | 4/2007 | Justis |
| 2007/0093816 A1 | 4/2007 | Arnin et al. |
| 2007/0100341 A1 | 5/2007 | Reqlos et al. |
| 2007/0118120 A1 | 5/2007 | Farris et al. |
| 2007/0118132 A1 | 5/2007 | Culbert et al. |
| 2007/0123861 A1 | 5/2007 | Dewey et al. |
| 2007/0123863 A1 | 5/2007 | Winslow et al. |
| 2007/0123989 A1 | 5/2007 | Gfeller et al. |
| 2007/0135814 A1 | 6/2007 | Farris |
| 2007/0161998 A1 | 7/2007 | Whipple |
| 2007/0167949 A1 | 7/2007 | Altarac et al. |
| 2007/0173828 A1 | 7/2007 | Firkins et al. |
| 2007/0213722 A1 | 9/2007 | Jones et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233079 A1 | 10/2007 | Fallin et al. |
| 2007/0239159 A1 | 10/2007 | Altarac et al. |
| 2007/0255284 A1 | 11/2007 | Miller et al. |
| 2007/0270811 A1 | 11/2007 | Dewey |
| 2007/0270867 A1 | 11/2007 | Miller et al. |
| 2007/0270868 A1 | 11/2007 | Dewey |
| 2007/0270869 A1 | 11/2007 | Young et al. |
| 2007/0276379 A1 | 11/2007 | Miller et al. |
| 2008/0009864 A1 | 1/2008 | Forton et al. |
| 2008/0015601 A1 | 1/2008 | Castro et al. |
| 2008/0039839 A1 | 2/2008 | Songer et al. |
| 2008/0045957 A1 | 2/2008 | Landry et al. |
| 2008/0051787 A1 | 2/2008 | Remington et al. |
| 2008/0065072 A1 | 3/2008 | Spitler et al. |
| 2008/0077136 A1 | 3/2008 | Triplett et al. |
| 2008/0077139 A1 | 3/2008 | Landry et al. |
| 2008/0077155 A1 | 3/2008 | Diederich et al. |
| 2008/0097441 A1 | 4/2008 | Hayes et al. |
| 2008/0177275 A1 | 7/2008 | Wing et al. |
| 2008/0183215 A1 | 7/2008 | Altarac et al. |
| 2008/0221626 A1 | 9/2008 | Butiers et al. |
| 2008/0228233 A1 | 9/2008 | Hoffman et al. |
| 2008/0234678 A1 | 9/2008 | Gutierrez et al. |
| 2008/0234765 A1 | 9/2008 | Frasier et al. |
| 2008/0243126 A1 | 10/2008 | Gutierrez et al. |
| 2008/0249372 A1 | 10/2008 | Reglos et al. |
| 2008/0249628 A1 | 10/2008 | Altarac et al. |
| 2008/0262554 A1 | 10/2008 | Hayes et al. |
| 2008/0306488 A1 | 12/2008 | Altarac et al. |
| 2008/0306489 A1 | 12/2008 | Altarac et al. |
| 2008/0306557 A1 | 12/2008 | Altarac et al. |
| 2008/0312692 A1 | 12/2008 | Brennan et al. |
| 2009/0030465 A1 | 1/2009 | Altarac et al. |
| 2009/0036929 A1 | 2/2009 | Reglos et al. |
| 2009/0082775 A1 | 3/2009 | Altarac et al. |
| 2009/0125032 A1 | 5/2009 | Gutierrez et al. |
| 2009/0125047 A1 | 5/2009 | Reglos et al. |
| 2009/0138056 A1 | 5/2009 | Anderson et al. |
| 2009/0177196 A1 | 7/2009 | Zlock et al. |
| 2009/0204155 A1 | 8/2009 | Aschmann |
| 2009/0216237 A1 | 8/2009 | Frezal et al. |
| 2009/0228045 A1 | 9/2009 | Hayes et al. |
| 2009/0228053 A1 | 9/2009 | Kolb et al. |
| 2009/0228054 A1 | 9/2009 | Hoffman et al. |
| 2009/0228055 A1 | 9/2009 | Jackson |
| 2010/0036423 A1 | 2/2010 | Hayes et al. |
| 2010/0174317 A1 | 7/2010 | Timm et al. |
| 2010/0222819 A1 | 9/2010 | Timm et al. |
| 2011/0144701 A1 | 6/2011 | Altarac et al. |
| 2011/0166610 A1 | 7/2011 | Altarac et al. |
| 2012/0089191 A1 | 4/2012 | Altarac et al. |

FOREIGN PATENT DOCUMENTS

| | | |
|---|---|---|
| EP | 0986339 | 3/2000 |
| EP | 1056408 | 12/2000 |
| EP | 1138268 | 10/2001 |
| EP | 1145602 | 10/2001 |
| EP | 1303225 | 4/2003 |
| EP | 1399078 | 3/2004 |
| EP | 1415602 | 7/2005 |
| EP | 1415603 | 7/2005 |
| EP | 1128773 | 6/2006 |
| EP | 1459690 | 6/2006 |
| EP | 986338 | 7/2006 |
| EP | 1810624 | 7/2007 |
| FR | 2728454 | 6/1996 |
| WO | 9116018 | 10/1991 |
| WO | 9426192 | 11/1994 |
| WO | 9531158 | 11/1995 |
| WO | 9600049 | 1/1996 |
| WO | 9822033 | 5/1998 |
| WO | 9848717 | 11/1998 |
| WO | 9855038 | 12/1998 |
| WO | 0062684 | 10/2000 |
| WO | 0130248 | 5/2001 |
| WO | 0141681 | 6/2001 |
| WO | 0238060 | 5/2002 |
| WO | 02065954 | 8/2002 |
| WO | 02067793 | 9/2002 |
| WO | 02076315 | 10/2002 |
| WO | 02102259 | 12/2002 |
| WO | 03047442 | 6/2003 |
| WO | 03075805 | 9/2003 |
| WO | 03094699 | 11/2003 |
| WO | 03101350 | 12/2003 |
| WO | 2004008949 | 1/2004 |
| WO | 2004047617 | 6/2004 |
| WO | 2004078221 | 9/2004 |
| WO | 2004103227 | 12/2004 |
| WO | 2004103228 | 12/2004 |
| WO | 2005009301 | 2/2005 |
| WO | 2005013864 | 2/2005 |
| WO | 2005018471 | 3/2005 |
| WO | 2005030029 | 4/2005 |
| WO | 2005030031 | 4/2005 |
| WO | 2005030066 | 4/2005 |
| WO | 2005030067 | 4/2005 |
| WO | 2005030087 | 4/2005 |
| WO | 2005041799 | 5/2005 |
| WO | 2005044152 | 5/2005 |
| WO | 2005046515 | 5/2005 |
| WO | 2005053572 | 6/2005 |
| WO | 2005055874 | 6/2005 |
| WO | 2005060879 | 7/2005 |
| WO | 2005067824 | 7/2005 |
| WO | 2005070278 | 8/2005 |
| WO | 2005070349 | 8/2005 |
| WO | 2005070350 | 8/2005 |
| WO | 2005070351 | 8/2005 |
| WO | 2005070352 | 8/2005 |
| WO | 2005070353 | 8/2005 |
| WO | 2005070354 | 8/2005 |
| WO | 2005076974 | 8/2005 |
| WO | 2005077113 | 8/2005 |
| WO | 2005079426 | 9/2005 |
| WO | 2005079672 | 9/2005 |

| | | |
|---|---|---|
| WO | 2005079711 | 9/2005 |
| WO | 2005084590 | 9/2005 |
| WO | 2005087121 | 9/2005 |
| WO | 2005092223 | 10/2005 |
| WO | 2005094704 | 10/2005 |
| WO | 2005096974 | 10/2005 |
| WO | 2005104998 | 11/2005 |
| WO | 2005117765 | 12/2005 |
| WO | 2005120401 | 12/2005 |
| WO | 2006016371 | 2/2006 |
| WO | 2006017507 | 2/2006 |
| WO | 2006023683 | 3/2006 |
| WO | 2006033659 | 3/2006 |
| WO | 2006039260 | 4/2006 |
| WO | 2006042188 | 4/2006 |
| WO | 2006042189 | 4/2006 |
| WO | 2006023671 | 5/2006 |
| WO | 2006047363 | 5/2006 |
| WO | 2006063083 | 6/2006 |
| WO | 2006063107 | 6/2006 |
| WO | 2006065774 | 6/2006 |
| WO | 2006067790 | 6/2006 |
| WO | 2006045091 | 8/2006 |
| WO | 2006055186 | 8/2006 |
| WO | 2006089237 | 8/2006 |
| WO | 2006096351 | 9/2006 |
| WO | 2006096381 | 9/2006 |
| WO | 2006101655 | 9/2006 |
| WO | 2006102268 | 9/2006 |
| WO | 2006102443 | 9/2006 |
| WO | 2006104999 | 10/2006 |
| WO | 2006108067 | 10/2006 |
| WO | 2006109310 | 10/2006 |
| WO | 2006110796 | 10/2006 |
| WO | 2006113256 | 10/2006 |
| WO | 2006115954 | 11/2006 |
| WO | 2006116214 | 11/2006 |
| WO | 2006119151 | 11/2006 |
| WO | 2006119236 | 11/2006 |
| WO | 2006119237 | 11/2006 |
| WO | 2006119241 | 11/2006 |
| WO | 2006125142 | 11/2006 |
| WO | 2006135511 | 12/2006 |
| WO | 2007014119 | 2/2007 |
| WO | 2007021588 | 2/2007 |
| WO | 2007031998 | 3/2007 |
| WO | 2007034472 | 3/2007 |
| WO | 2007037801 | 4/2007 |
| WO | 2007038261 | 4/2007 |
| WO | 2007043044 | 4/2007 |
| WO | 2007075375 | 7/2007 |
| WO | 2007102846 | 9/2007 |
| WO | 2007117366 | 10/2007 |
| WO | 2007121061 | 10/2007 |
| WO | 2007127608 | 11/2007 |
| WO | 2007127682 | 11/2007 |
| WO | 2007136612 | 11/2007 |
| WO | 2008069835 | 6/2008 |
| WO | 2008115549 | 9/2008 |
| WO | 2008121343 | 10/2008 |
| WO | 2008121421 | 10/2008 |
| WO | 2008124186 | 10/2008 |
| WO | 2008140756 | 11/2008 |
| WO | 2008153747 | 12/2008 |
| WO | 2009042489 | 4/2009 |
| WO | 2009049206 | 4/2009 |
| WO | 2009076239 | 6/2009 |
| WO | 2009091960 | 7/2009 |
| WO | 2009100190 | 8/2009 |
| WO | 2010019791 | 2/2010 |
| WO | 2011017712 | 2/2011 |
| WO | 2011028575 | 3/2011 |

OTHER PUBLICATIONS

USPTO Final Office Action for U.S. Appl. No. 11/586,849, mailed Jan. 6, 2012.
USPTO Final Office Action for U.S. Appl. No. 12/355,093, mailed Dec. 13, 2011.
USPTO Non-Final Office Action for U.S. Appl. No. 12/270,505, mailed Feb. 16, 2012.
Extended European Search Report for European Patent Application No. 06788250.6, mailed Feb. 27, 2012. (6 pages).
First Examiner's Report for Australian App. No. 2008229323 mailed Jun. 24, 2012. (pp. 4).
Extended European Search Report for European Patent Application No. 08742359.6, mailed Jun. 27, 2012. (5 pages).
First Examiner's Report for Australian App. No. 2007235543 mailed Feb. 20, 2012. (pp. 2).
Extended European Search Report for European Patent Application No. 07794326.4, mailed Mar. 23, 2012. (6 pages).
USPTO Advisory Action for U.S. Appl. No. 11/586,849, mailed Mar. 15, 2012.
USPTO Notice of Allowance for U.S. Appl. No. 11/726,093, mailed May 10, 2012.
USPTO Advisory Action for U.S. Appl. No. 12/355,093, mailed Mar. 9, 2012.
USPTO Final Office Action for U.S. Appl. No. 12/270,505, mailed Jul. 19, 2012.
USPTO Non-Final Office Action for U.S. Appl. No. 12/853,260, mailed Jul. 13, 2012.
USPTO Notice of Allowance for U.S. Appl No. 11/362,366 mailed Mar. 6, 2012.
USPTO Final Office Action for U.S. Appl. No. 11/726,093, mailed May 12, 2011.
Co-Pending U.S. Appl. No. 11/427,738 by Reglos et al entitled "Systems and Methods for Stabilization of Bone Structures", filed Jun. 29, 2006.
Co-Pending U.S. Appl. No. 11/436,407 by Hayes et al entitled "Systems and Methods for Posterior Dynamic Stabilization of the Spine", filed May 17, 2006.
First Examiner's Report for AU App. No. 2006272755 mailed May 31, 2011. (pp. 1-3).
Second Exmainer's Report for AU App. No. 2005295209 mailed Jun. 1, 2011. (pp. 1-3).
International Preliminary Report on Patentability and Written Opinion for PCT/US2008/004098, mailed Jul. 25, 2008. (pp. 1-7).
International Preliminary Report on Patentability and Written Opinion for PCT/US2008/03677, mailed Jul. 22, 2008. (pp. 1-9).
International Preliminary Report on Patentability and Written Opinion for PCT/US2008/079580, mailed Apr. 29, 2009. (pp. 1-6).
International Preliminary Report on Patentability and Written Opinion for PCT/US2009/053740, Feb. 21, 2011. (6 pages).
International Search Report and Written Opinion for PCT/US2006/28586, mailed Jul. 27, 2007. (pp. 1-14).
International Search Report and Written Opinion for PCT/US2005/038021, mailed Apr. 10, 2006 (pp. 1-6).
International Search Report and Written Opinion for PCT/US2007/004726, mailed Jul. 8, 2008. (pp. 1-6).
International Search Report and Written Opinion for PCT/US2007/11573, mailed Apr. 23, 2008. (pp. 1-6).
International Search Report and Written Opinion for PCT/US2008/085748, mailed Jun. 22, 2009. (pp. 1-10).
USPTO Communicaiton for U.S. Appl. No. 11/362,366 mailed Mar. 18, 2011.
International Search Report for PCT/US2008/004098, mailed Jul. 25, 2008. (1 page).
International Search Report for PCT/US2008/03677, mailed Jul. 22, 2008. (1 page).
International Search Report for PCT/US2008/079580, mailed Apr. 29, 2009. (pp. 1-5).
International Search Report for PCT/US2009/053740, mailed Mar. 24, 2010. (pp. 1-4).
International Search Report for PCT/US2010/44930, mailed Apr. 1, 2011. (pp. 1-4).
Written Opinion for PCT/US2010/44930, mailed Mar. 31, 2009. (pp. 1-4).
USPTO Communicaiton for U.S. Appl. No. 10/970,366 mailed Nov. 25, 2008.
USPTO Communicaiton for U.S. Appl. No. 10/970,366 mailed Nov. 5, 2009.

USPTO Communicaiton for U.S. Appl. No. 11/006,495 mailed Dec. 29, 2009.
USPTO Communicaiton for U.S. Appl. No. 11/006,495 mailed Jun. 6, 2008.
USPTO Communicaiton for U.S. Appl. No. 11/006,495 mailed Mar. 20, 2009.
USPTO Communicaiton for U.S. Appl. No. 11/033,452 mailed Dec. 11, 2008.
USPTO Communicaiton for U.S. Appl. No. 11/033,452 mailed Oct. 13, 2009.
USPTO Communicaiton for U.S. Appl. No. 11/427,738 mailed Dec. 29, 2009.
USPTO Communication for U.S. Appl. No. 11/436,407 mailed Jun. 21, 2009.
USPTO Communication for U.S. Appl. No. 11/006,495 mailed Jun. 30, 2008.
Co-Pending U.S. Appl. No. 11/586,849 by Altarac et al entitled "Systems and methods for stabilization of bone structures", filed Oct. 25, 2006.
USPTO Communicaiton for U.S. Appl. No. 11/586,849, mailed Jul. 8, 2011.
Co-Pending U.S. Appl. No. 11/726,093 by Altarac et al entitled "Screw systems and methods for use in stabilization of bone structures", filed Mar. 20, 2007.
USPTO Communication for U.S. Appl. No. 11/726,093, mailed Nov. 5, 2010.
USPTO Communication for U.S. Appl. No. 11/726,093, mailed May 12, 2011.
USPTO Communicaiton for U.S. Appl. No. 11/362,366 mailed Apr. 23, 2010.
USPTO Communicaiton for U.S. Appl. No. 11/362,366 mailed Apr. 7, 2009.
Co-Pending U.S. Appl. No. 12/966,807 by Altarac et al entitled "Methods for Stabilization of Bone Structures", filed Dec. 13, 2010.
Co-Pending U.S. Appl. No. 12/966,790 by Altarac et al entitled "Method for Stabilizing Bone Strucutres", filed Dec. 13, 2010.
Co-Pending U.S. Appl. No. 12/077,462 by Gutierrez et al entitled "Rod reducer", filed Mar. 19, 2008.
USPTO Communication for U.S. Appl. No. 12/077,462, mailed Mar. 18, 2011.
Co-Pending U.S. Appl. No. 12/329,423 by Altarac et al entitled "Spondylolisthesis reduction system and method", filed Dec. 5, 2008.
Co-Pending U.S. Appl. No. 12/270,505 by Gutierrez et al entitled "Rod removal instrument", filed Nov. 13, 2008.
Co-Pending U.S. Appl. No. 12/853,260 by Altarac et al entitled "Systems and Methods for Stabilization of Bone Structures, Including Thorocolumbar Stabilization Systems and Methods", filed Aug. 9, 2010.
Co-pending U.S. Appl. No. 11/362,366 by Altarac et al. entitled "Systems and methods for stabilization of bone structures", filed Feb. 23, 2006.
USPTO Advisory Action for U.S. Appl. No. 11/726,093, mailed Aug. 30, 2011.
USPTO Notice of Allowance for U.S. Appl. No. 12/077,462, mailed Sep. 28, 2011.
USPTO Final Office Action for U.S. Appl. No. 11/362,366 mailed Oct. 27, 2011.
USPTO Non-Final Office Action for U.S. Appl. No. 12/329,423, mailed Nov. 30, 2011.
USPTO Non-Final Office Action for U.S. Appl. No. 11/362,366 mailed Mar. 18, 2011.
Second Examiner's Report for Australian App. No. 2006272755 mailed Jun. 20, 2012. (pp. 3).
First Examiner's Report for Australian App. No. 2008233124 mailed Sep. 20, 2012. (pp. 6).
USPTO Non-Final Office Action for U.S. Appl. No. 12/355,093, mailed Aug. 16, 2012.
USPTO Non-Final Office Action for U.S. Appl. No. 12/966,807, mailed Nov. 9, 2012.
USPTO Non-Final Office Action for U.S. Appl. No. 12/355,093, mailed Jan. 23, 2013.
USPTO Non-Final Office Action for U.S. Appl. No. 12/966,790, mailed Mar. 6, 2013.
USPTO Final Office Action for U.S. Appl. No. 12/853,260, mailed Jan. 24, 2013.
USPTO Notice of Allowance for U.S. Appl. No. 12/355,093, mailed May 29, 2013.
USPTO Notice of Allowance for U.S. Appl. No. 12/966,807, mailed May 28, 2013.

* cited by examiner

TISSUE SPLITTER

CROSS-REFERENCE TO RELATED APPLICATIONS

This application claims priority to and the benefit of and is a continuation-in-part of U.S. Provisional Patent Application Ser. No. 61/011,478 entitled "Tissue splitter" filed on Jan. 16, 2008 and is incorporated herein by reference in its entirety. This application is a continuation-in-part of U.S. patent application Ser. No. 11/586,849 entitled "Systems and methods for stabilization of bone structures" filed on Oct. 25, 2006 which is a continuation-in-part of U.S. patent application Ser. No. 11/362,366 entitled "Systems and methods for stabilization of bone structures" filed on Feb. 23, 2006 which is a non-provisional of U.S. Provisional Patent Application 60/701,660 entitled "Systems and methods for stabilization of bone structures" filed on Jul. 22, 2005, all of these applications are hereby incorporated by reference in their entireties.

BACKGROUND

Damage to the spine as a result of advancing age, disease, and injury, has been treated in many instances by fixation or stabilization of vertebrae. Conventional methods of spinal fixation utilize a rigid or semi-rigid spinal fixation device to support an injured spinal vertebra relative to an adjacent vertebra and prevent movement of the injured vertebra relative to an adjacent vertebra. These conventional spinal fixation devices include anchor members for fixing to a series of two or more vertebrae of the spine and at least one substantially rigid link element designed to interconnect the anchor members. Typically, the anchor member is a screw and the substantially rigid link element is a rod. The screw is configured to be inserted into the pedicle of a vertebra to a predetermined depth and angle. One end of the rigid link element is connected to an anchor inserted in the pedicle of the upper vertebra and the other end of the rod is connected to an anchor inserted in the pedicle of an adjacent lower vertebra. The rod ends are connected to the anchors via coupling constructs such that the adjacent vertebrae are supported and held apart in a relatively fixed position by the rods. Typically, two rods and two pairs of anchors are installed each in the manner described above such that two rods are employed to fix two adjacent vertebrae, with one rod positioned on each side of adjacent vertebrae. Once the system has been assembled and fixed to a series of two or more vertebrae, it constitutes a rigid device preventing the vertebrae from moving relative to one another. This rigidity enables the devices to support all or part of the stresses instead of the stresses being born by the series of damaged vertebra.

The implantation of a rod requires a pathway to be created through the surrounding tissue between two anchors. Because of the surrounding tissue between two anchors is comprised of muscle and fascia, the pathway, if not cleared, makes passing the rod through muscle and fascia quite difficult. Therefore, there is a need for instrumentation designed to create a pathway for rod implantation. Furthermore, in minimally invasive procedures, the pathway preferably needs to be cleared subcutaneously to minimize the disruption and damage to the surrounding tissue. Therefore, the need extends to instrumentation designed to create a pathway subcutaneously for rod implantations. The present invention sets forth such instrumentation.

SUMMARY

According to one aspect of the invention, an instrument is provided comprising a shaft, an actuator connected to the shaft and a blade connected to the distal end of the actuator. The actuator is configured to extend and retract the blade with respect to the shaft and the shaft is configured to be insertable into a cannula having a longitudinal axis and connectable to the cannula such that the blade is capable of longitudinal movement with respect to the cannula. The longitudinal movement with respect to the cannula is controllable and adjustable by the instrument having adjustable stops such that the cut created by the longitudinal movement does not breach the skin.

According to another aspect of the invention, an instrument comprising a retractable blade at a distal end is provided. The instrument is configured to be insertable into a cannula with the blade in a retracted state. The blade is movable subcutaneously by a distance relative to the cannula to create a subcutaneous cut outside the cannula.

According to another aspect of the invention, a system is provided. The system includes a first cannula connectable to a first bone anchor implanted in a first vertebral body. The first cannula has a longitudinal sidewall opening. A second cannula is connectable to a second bone anchor implanted in a second vertebral body. The system includes an instrument insertable into the first cannula. The instrument includes a shaft, an actuator connected to the shaft, and a blade connected to the distal end of the actuator. The actuator is configured to move the blade through the longitudinal sidewall opening into a deployed configuration such that the blade projects through the longitudinal sidewall opening towards the second cannula and the blade is longitudinally movable inside the longitudinal sidewall opening of the cannula by a distance to subcutaneously cut tissue outside the cannula.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. All figures herein illustrate a tissue splitter according to the present invention.

DETAILED DESCRIPTION

Figure 1A:
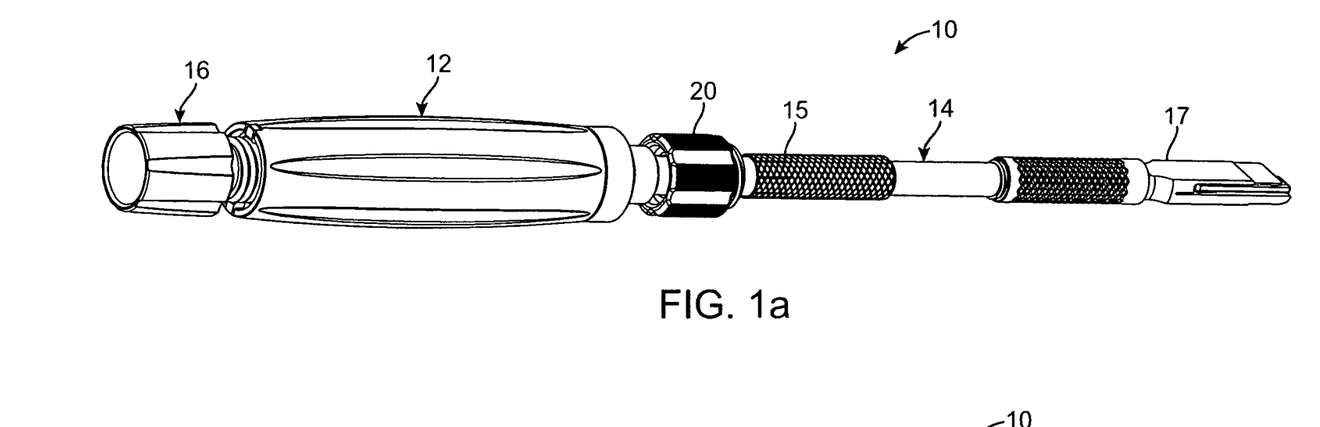
FIG. 1a illustrates a perspective view of a tissue splitter according to the present invention.
Figure 1B:
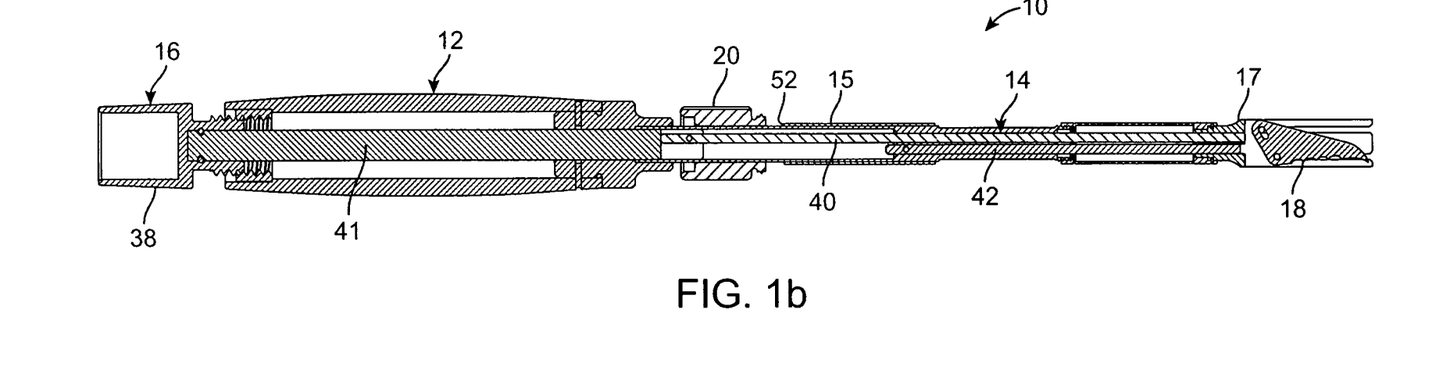
FIG. 1b illustrates a cross-sectional view of a tissue splitter according to the present invention.

With reference to FIGS. 1a and 1b, there is shown a tissue splitter 10 according to the present invention. The tissue splitter 10 includes a handle assembly 12 connected to a shaft assembly 14 and an actuator assembly 16 connected to a blade 18 and an adjustment collar 15 and locking collar 20 connected to the shaft assembly 14. The locking collar 20 is placed over the shaft assembly 14 and permitted to free-float between an adjustment collar 15 and the handle assembly 12. The distal end of the locking collar 20 includes a threaded portion for connecting or locking the locking collar 20 and in turn, the tissue splitter 10 to a cannula or other instrument. An adjustment collar 15 is connected to the shaft assembly 14 and also permitted to slide and be locked with respect to the shaft assembly 14.

Figure 2A:
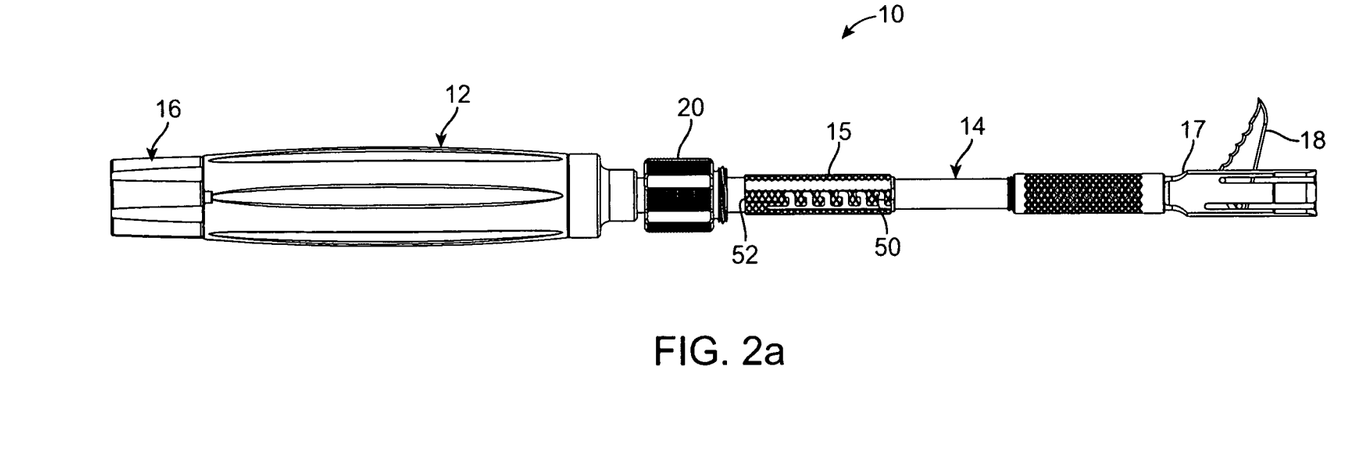
FIG. 2a illustrates a side view of a tissue splitter with blade extended according to the present invention.
Figure 3A:
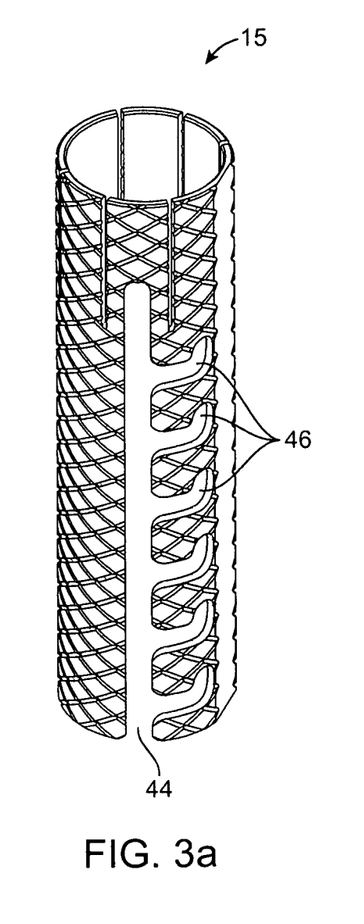
FIG. 3a illustrates a perspective view of an adjustment collar according to the present invention.
Figure 3B:
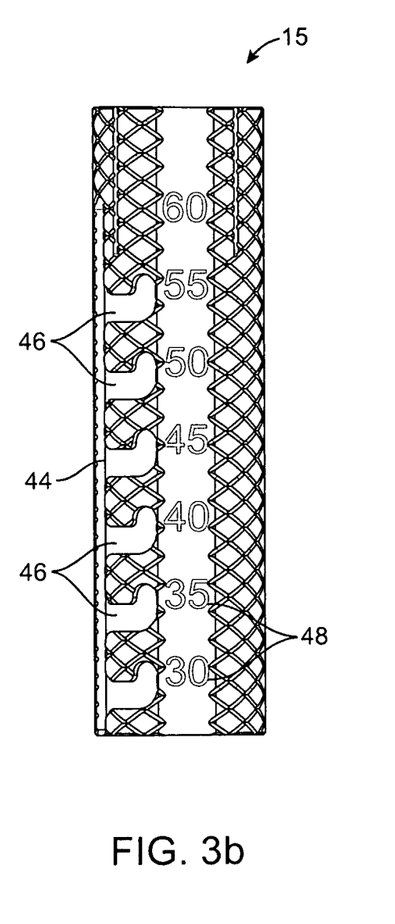
FIG. 3b illustrates a side view of an adjustment collar according to the present invention.

Referring briefly to FIGS. 3a and 3b, there is shown an adjustment collar 15 according to the present invention. The adjustment collar 15 is substantially cylindrical in shape and includes a longitudinal slot 44 formed in the sidewall with a plurality of side slots 46 having corresponding adjacent graduations 48. The adjacent graduations 48 correspond to various and approximate lengths of spinal stabilization rods implantable between two bone anchors placed in vertebral bodies. A pin 50 (seen in FIG. 2a) formed on the outer surface of the shaft assembly 14 is configured to travel the longitudinal slot 44 relative to the adjustment collar 15 to position the adjustment collar 15 relative to the shaft assembly 14 or the locking collar 20 by a distance approximately equal to the length of a rod selected for implantation. Hence, the adjustment collar 15 is movable with respect to the shaft 14 and its position adjusted and locked from said movement by guiding the pin 50 into any of the side slots 46. For example, after a surgeon measures the pedicle-to-pedicle distance of adjacent vertebrae and determines the rod length suitable for implantation to be 45 mm, the surgeon will slide the adjustment collar 15 longitudinally relative to the shaft assembly 14 such that the pin 50 travels in the longitudinal slot 44. Then, the surgeon will turn the adjustment collar 15 to position the pin 50 in the side slot 46 having the appropriate graduation "45" inscribed next to the side slot 46. So positioned, the pin 50 is approximately the rod length distance from the distal end of the locking collar 20 when connected to a cannula or other instrument through which the instrument is inserted. Hence, a stop is defined by the adjustment collar 15 against which movement of the blade 18 is limited to prevent the blade 18 from breaching skin from its subcutaneous position when creating a cut.

Referring back to FIGS. 1 and 2, a blade housing assembly 17 is connected to the shaft assembly 14. In one variation, the blade housing assembly 17 is threadingly connected to the shaft assembly 14 such that rotation of the proximal end of the blade housing assembly 17 permits the blade housing assembly 17 to longitudinally slide proximally on the shaft assembly 14 to expose, remove and exchange the blade 18. The blade housing assembly 17 is moved distally longitudinally to encase and cover the blade 18 with the proximal end of the blade housing assembly 17 rotated to threadingly re-connect the blade housing 17 to the shaft assembly 14. As a result, disposable blades may be employed.

Figure 2B:
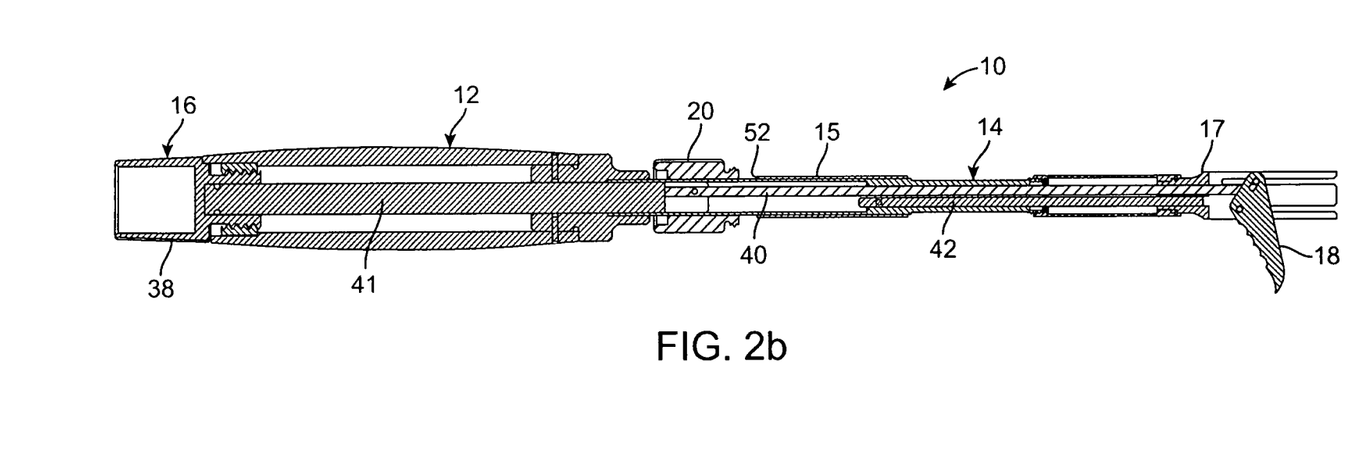
FIG. 2b illustrates a cross-sectional view of a tissue splitter with blade extended according to the present invention.

FIGS. 1a and 1b show the tissue splitter 10 in an undeployed configuration in which the blade 18 is retracted. FIGS. 2a and 2b show the tissue splitter 10 in a deployed configuration in which the blade 18 is extracted or deployed. With particular reference to FIGS. 1b and 2b, the actuator assembly 16 includes a proximal knob 38 connected to an inner shaft 41 which is connected to a back linkage 40 that is connected to the blade 18 which is in turn connected to a front linkage 42. The front linkage 42 is connected to the shaft assembly 14. The inner shaft 41 of the actuator assembly 16 is disposed inside the handle assembly 12. The actuator assembly 16 is in part disposed inside the shaft assembly 14. Rotation of the proximal knob 38 in one direction drives the shaft 41 and connected back linkage 40 toward the distal end of the instrument 10 relative to the handle and shaft assemblies 12, 14 pivoting the blade 18 out from the blade housing assembly 17. Rotation of the proximal knob 38 activates the blade 18 into deployment in which the blade 18 projects outwardly from the distal end of the instrument 10 to expose the blade 18. Rotation of the proximal knob 38 in the opposite direction draws the shaft 41 and connected back linkage 40 proximally, thereby, pivoting the blade 18 to within the confines of the blade housing assembly 17. Rotation of the proximal knob 38 in the opposite direction retracts the blade 18 into an undeployed or retracted position in which the blade 18 is hidden in the blade housing assembly 17. In the variation shown, a serrated blade 18 is employed to advantageously cut tissue when the blade 18 is moved. Also, in one variation, the blade 18 is angled with respect to the shaft assembly 14 or blade housing assembly 17 or cannula when in the extracted deployed state.

Figure 4:
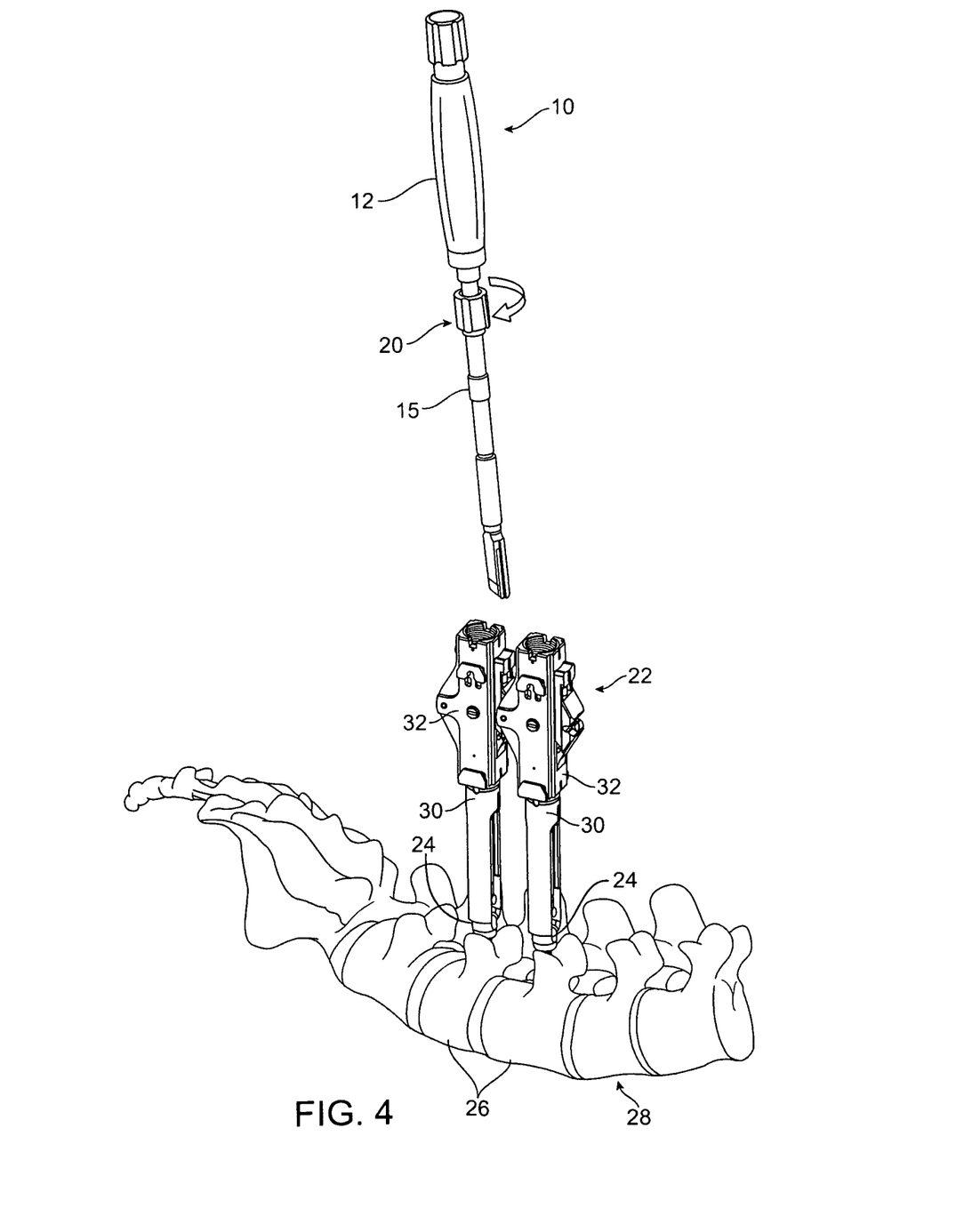
FIG. 4 illustrates a perspective view of a tissue splitter in conjunction with an access system connected to a pair of bone anchors implanted into adjacent vertebral bodies of a patient's spine shown in part.

Turning now to FIG. 4, there is shown the tissue splitter 10 in conjunction with a minimally invasive, percutaneous rod deployment system 22 attached to a pair of bone anchors 24 that are implanted into adjacent vertebral bodies 26 of a patient's spine 28 shown in part in FIG. 4. The minimally invasive, percutaneous rod deployment system 22, such as that developed by Vertiflex, Inc. and described in detail in U.S. patent application bearing Ser. No. 11/362,366 entitled "Systems and methods for stabilization of bone structures" filed on Feb. 23, 2006 and in U.S. patent application bearing Ser. No. 11/586,849 entitled "Systems and methods for stabilization of bone structures" filed on Oct. 25, 2006, both of which are incorporated herein by reference in their entireties, comprises, in part, of a pair of slotted cannulas 30 with alignment guides 32 seated on top of the cannulas 30. Prior to insertion of a rod, the rod length is determined by the clinician. Also, the outside of the cannulas 30 include depth markers 34 which can be read above the skin 36 (see FIG. 5). The depth that the cannulas are sunk into the patient is typically greater than the length of the rod to be implanted and as such, the cut that the tissue splitter 10 makes at the first cannula is preferably approximately equal to the length of the rod and less than the approximate depth to which the first cannula is sunk into the patient. The adjustment collar 15 is positioned with respect to the shaft assembly 14 by moving the pin 50 along the longitudinal slot 44 and into a side slot 46 that corresponds approximately to the desired length of the cut which may correspond to the length of the rod to be deployed and/or to less than the depth reading at the skin on the outside of the cannulas. In cases where the patient is thin, for example, a depth marking on the cannula may shown 35 millimeters and the surgeon selected rod length may be 45 millimeters. In such cases, the clinician would select the smaller cut, 35 millimeters, so as to not breach the skin. Prior to implantation of the rod, the tissue splitter 10 is inserted into a first alignment guide 32 that is connected to a first cannula 30 or in another variation, inserted into a cannula 30 without an alignment guide 32. The tissue splitter 10 is inserted such that the tissue splitter is aligned with a second cannula. Markers on the tissue splitter 10 are provided to aid the user in properly inserting and aligning the tissue splitter 10 into the first cannula 30. In general, a properly oriented tissue splitter 10 is one in which the blade is deployable in a direction toward the other or second cannula 30. The tissue splitter 10 is connected to the alignment guide 32 or directly to the cannula 30 via the locking collar 20 or other means. In one variation, the tissue splitter 10 is connected by rotation of the locking mechanism 20 which threads to a correspondingly threaded alignment guide 32 or cannula 30.

Figure 5:
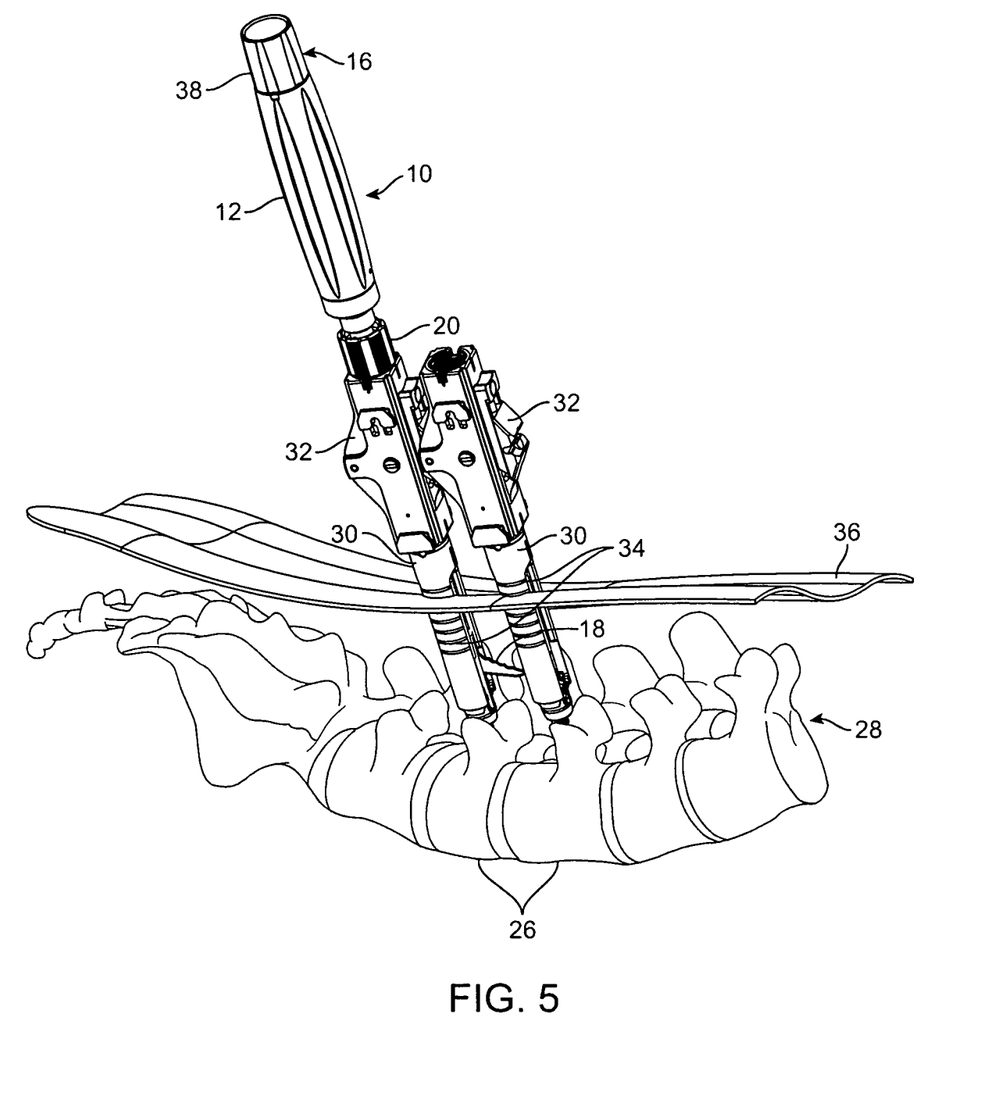
FIG. 5 illustrates a perspective view of a tissue splitter in conjunction with an access system extending through skin and connected to a pair of bone anchors implanted into adjacent vertebral bodies of patient's spine shown in part.
Figure 6A:
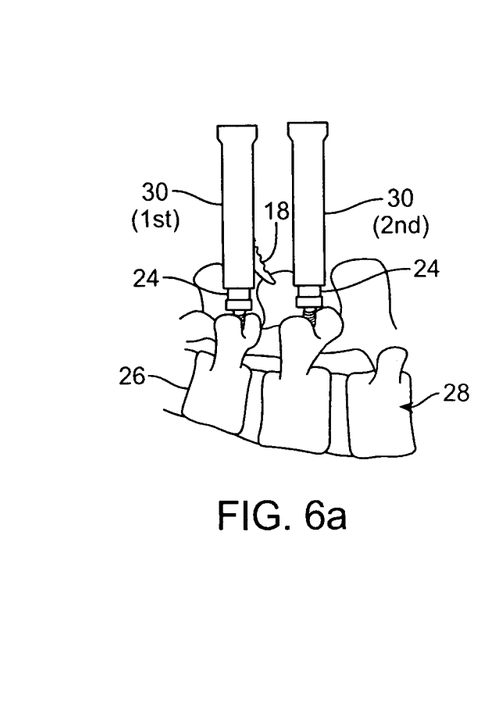
FIG. 6a illustrates a side view of a partially deployed blade of a tissue splitter inserted in one of two cannulas connected to bone anchors implanted in adjacent vertebral bodies of a patient's spine.
Figure 6B:
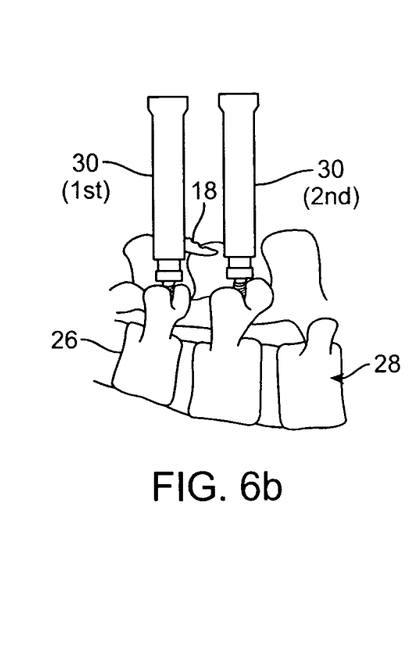
FIG. 6b illustrates a side view of a fully deployed blade of a tissue splitter inserted in one of two cannulas connected to bone anchors implanted in adjacent vertebral bodies of a patient's spine.
Figure 6C:
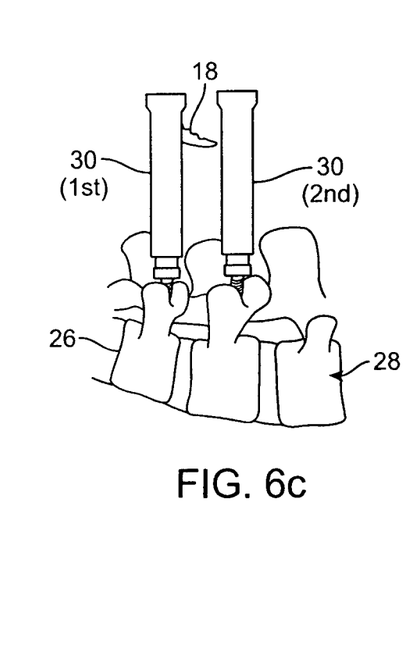
FIG. 6c illustrates a side view of a fully deployed blade of a tissue splitter inserted in one of two cannulas connected to bone anchors implanted in adjacent vertebral bodies of patient's spine with the blade pulled proximally to dissect tissue between the two cannulas.
Figure 7:
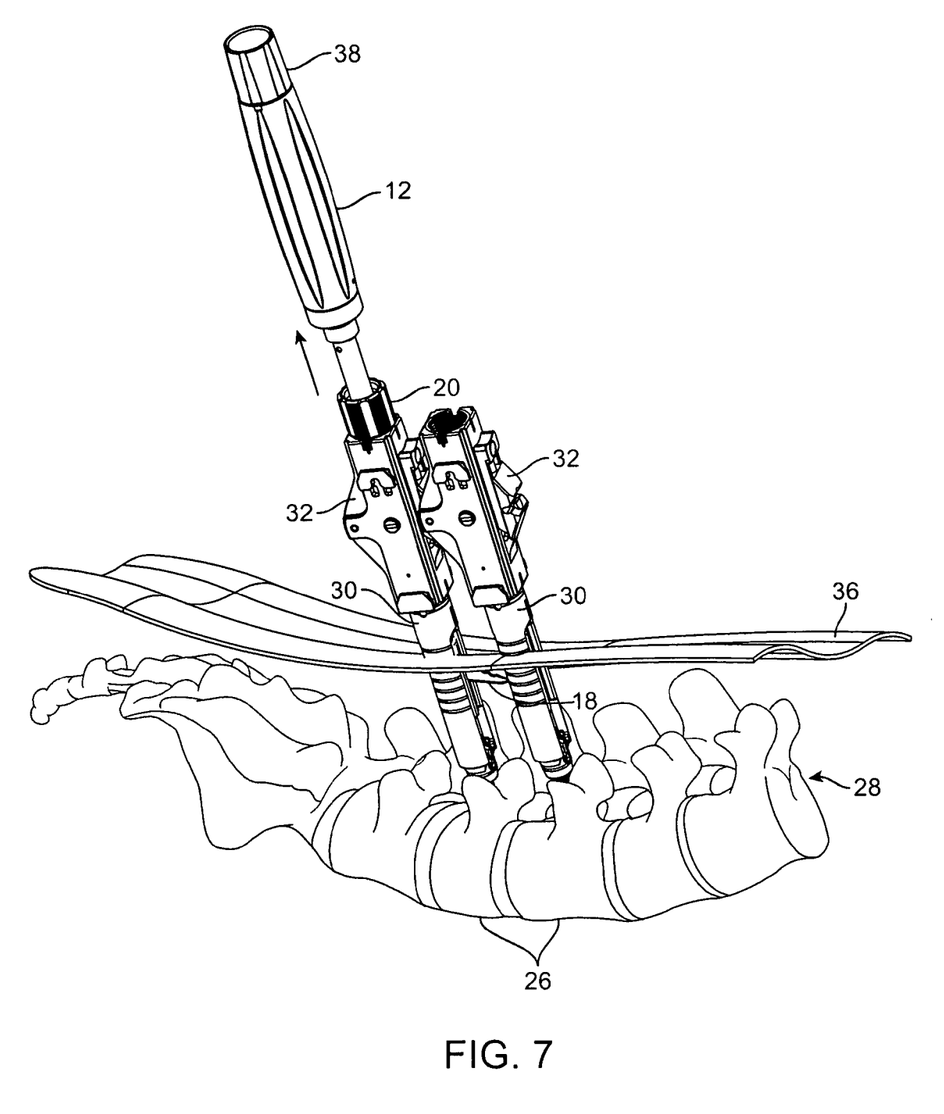
FIG. 7 illustrates a perspective view of a fully deployed blade of a tissue splitter inserted in one of two cannulas connected to bone anchors implanted in adjacent vertebral bodies of patient's spine with the blade pulled proximally to dissect tissue subcutaneously between the two cannulas.

Still referencing FIG. 5 and turning to FIGS. 6a-6c, the blade 18 is actuated and deployed by turning the proximal knob 38 of the actuator assembly 16. The blade 18 may be actuated by other means known to one skilled in the art including a push type mechanism for deploying the blade. As a result, the blade 18 emerges from the blade housing assembly 17 and through the slot in the first cannula 30 and begins to cut tissue as shown in FIG. 6a. In FIG. 6b, the blade 18 is shown fully deployed. In FIG. 6c and FIG. 7, the handle assembly 12 is pulled upwardly by the user in a longitudinal direction as shown by the arrow in FIG. 7 along the cannula inside the cannula slot. As a result of pulling the handle assembly 12 upwardly, the handle assembly 12 that is connected to the shaft assembly 14 which is in turn connected to the blade housing assembly 17 pulls the deployed blade 18 upwardly, thereby, cutting more tissue in an upwardly direction as shown in FIG. 7 and shown progressively in FIGS. 6a-6c. The handle assembly 12 can then be pushed distally and pulled again to repeat the cutting motion as needed. Upward translation of the blade 18 is limited by at least one stop relative to the cannula. Downward translation of the blade 18 in one variation is also limited by at least one stop. Also, after a cut is made with the tissue splitter 10 in the first cannula, it may be removed and placed into the second cannula and a second cut made. The second cut the same length or the adjustment collar 15 may be adjusted for a shorter cut, which may be determined by the clinician as necessary where skin depth is smaller than the desired rod length or when rod length is longer than the blade length.

The locking collar 20 which is connected to the alignment guide 32 is free-floating with respect to the shaft assembly 14 allowing the shaft assembly 14 to translate longitudinally within the locking collar 20 between a first stop and a second stop, thereby, limiting longitudinal blade movement. One stop is defined by the adjustment collar 15 which, in one variation, is the proximal end 52 of the adjustment collar 15, against which a stop defined by the locking collar 20 abuts arresting further longitudinal translation in the proximal direction of the shaft/blade relative to the locking collar 20. In one variation, another stop is defined the handle assembly 12 which, in one variation, is the distal end of the handle assembly 12 against which a stop defined by the locking collar 20 abuts arresting further longitudinal translation in the distal direction of the shaft/blade relative to the locking collar 20. The blade 18 is allowed limited longitudinally travel relative to the cannula between two stops that are defined by the instrument. One of the stops is adjustable by the user such as the adjustment collar to customly vary the distance traveled by the blade relative to the cannula so as to not breach skin and maintain a subcutaneous incision. The adjustment collar 15 can be moved and locked into position with respect to the shaft assembly 14 and as such the movable adjustment collar 15 advantageously adjusts the distance between the first stop that is defined by the adjustment collar 15 and a second stop. The first and second stops between which the locking collar 20 is allowed to move also limits travel of the blade 18 with respect to the locking collar 20 which when connected to the cannula limits travel of the blade 18 in turn with respect to the cannula 30 as well, thereby, preventing the blade from breaching the skin surface or cutting a length that is too long. The position of the alignment collar 15 is selected to the length of the cut according to the length of the rod to be implanted and/or marker readings on the outside of the cannulas. Adjusting the position of the alignment collar 15 translates the alignment collar 15 along the shaft assembly 14 which thereby varies the stop defined by the alignment collar 15 and hence the travel distance of the shaft and handle assemblies with respect to the locking collar 20.

As shown in FIGS. 6a-6c, the blade 18 is angled downwardly towards the second cannula 30. Also, the blade 18 is also wider proximate to its point of attachment relative to the distal end of the blade which is narrower. As a result of this angle and width of blade, the length of the cut created by the tissue splitter near the first cannula is longer relative to the length of the cut created by the tissue splitter 10 near the first cannula 30. This length differential is advantageous because the rod is first seated in the first bone anchor and rotated through a slot in the first cannula towards the second cannula. As a result of the rotation of the rod having a pivot point at the first anchor, an arc is traced by the rod that requires a shorter cut near the second cannula where the arc ends relative to near the first cannula where the rod is in a substantially vertical orientation inside the first cannula and begins to arc and therefore requires a longer cut or pathway. If needed, the tissue splitter can be placed on the second alignment guide and tissue can be further dissected. With the tissue splitter removed, the rod is inserted into one of the first or second cannulas and rotated through the slotted cannula toward the other of the first or second cannula and connected to the first and second bone anchors.

All publications mentioned herein are incorporated herein by reference to disclose and describe the methods and/or materials in connection with which the publications are cited. Although preferred illustrative embodiments of the present invention are described hereinabove, it will be apparent to those skilled in the art that various changes and modifications may be made thereto without departing from the invention. It is intended in the appended claims to cover all such changes and modifications that fall within the true spirit and scope of the invention.

We claim:

1. An instrument comprising:
a shaft;
an actuator connected to the shaft;
a blade connected to the distal end of the actuator;
wherein the actuator is configured to extend and retract the blade with respect to the shaft; and
wherein the shaft is configured to be insertable into a cannula having a longitudinal axis and connectable to the cannula such that the blade is capable of longitudinal movement with respect to the cannula;
a locking collar connected to the shaft such that the shaft is capable of longitudinal movement with respect to the locking collar; the locking collar being configured to connect to the cannula such that the instrument is inhibited from removal from the cannula;

an adjustment collar connected to the shaft; the adjustment collar being longitudinally movable with respect to the shaft, wherein the longitudinal movement of the blade with respect to the cannula is limited by a plurality of predetermined stops defined by the adjustment collar.

2. The instrument of claim 1, wherein the longitudinal movement of the shaft is limited by a stop defined by the locking collar.

3. The instrument of claim 1 wherein the shaft is insertable into a cannula having a longitudinal opening in the sidewall of the cannula; the shaft is connectable to the cannula such that the blade is extendable through the longitudinal opening of the cannula and longitudinally movable inside the longitudinal opening of the cannula.

4. The instrument of claim 1, wherein a portion of the adjustment collar engages, during use, a portion of the locking collar such that longitudinal movement of the shaft in a first direction is limited.

5. The instrument of claim 1, wherein the instrument is adapted for creating a subcutaneous pathway for a spinal stabilization rod.

6. The instrument of claim 1, wherein the blade is angled with respect to the cannula when in an extracted state.

7. An instrument comprising:
a shaft;
an actuator connected to the shaft;
a blade connected to the distal end of the actuator;
wherein the actuator is configured to extend and retract the blade with respect to the shaft; and
wherein the shaft is configured to be insertable into a cannula having a longitudinal axis and connectable to the cannula such that the blade is capable of longitudinal movement with respect to the cannula;
a locking collar connected to the shaft such that the shaft is capable of longitudinal movement with respect to the locking collar; the locking collar being configured to connect to the cannula such that the instrument is inhibited from removal from the cannula;
an adjustment collar connected to the shaft; the adjustment collar being longitudinally movable with respect to the shaft, wherein the longitudinal movement of the blade with respect to the cannula is limited by a plurality of predetermined stops defined by the adjustment collar, and wherein at least one of the predetermined stops defined by the adjustment collar defines the distance to be approximately less than the length of a spinal stabilization rod.

8. The instrument of claim 7, wherein the longitudinal movement of the shaft is limited by a stop defined by the locking collar.

9. The instrument of claim 7, wherein the shaft is insertable into a cannula having a longitudinal opening in the sidewall of the cannula; the shaft is connectable to the cannula such that the blade is extendable through the longitudinal opening of the cannula and longitudinally movable inside the longitudinal opening of the cannula.

10. The instrument of claim 7, wherein a portion of the adjustment collar engages, during use, a portion of the locking collar such that longitudinal movement of the shaft in a first direction is limited.

11. The instrument of claim 10, further comprising a handle connected to the shaft, wherein a portion of the handle engages, during use, a portion of the locking collar such that longitudinal movement of the shaft in a second direction is limited, and wherein the second direction is in a direction substantially opposite to the first direction.

12. The instrument of claim 7, wherein the instrument is adapted for creating a subcutaneous pathway for a spinal stabilization rod.

13. The instrument of claim 7, wherein the blade is angled with respect to the cannula when in an extracted state.

14. A system comprising:
a first cannula connectable to a first bone anchor implanted in a first vertebral body; the first cannula having a longitudinal sidewall opening;
a second cannula connectable to a second bone anchor implanted in a second vertebral body;
an instrument insertable into the first cannula; the instrument comprising:
a shaft;
an actuator connected to the shaft;
a blade connected to the distal end of the actuator;
wherein the actuator is configured to move the blade through the longitudinal sidewall opening into a deployed configuration such that the blade projects through the longitudinal sidewall opening towards the second cannula; and the blade being longitudinally movable inside the longitudinal sidewall opening of the cannula by a distance to subcutaneously cut tissue outside the cannula;
a locking collar connected to the shaft such that the shaft is longitudinally movable with respect to the locking collar; the instrument being connectable to the first cannula via the locking collar such that the instrument is inhibited from removal from the first cannula; and
an adjustment collar connected to the shaft; the adjustment collar being longitudinally movable with respect to the shaft, wherein the longitudinal movement of the blade with respect to the first cannula is limited by a plurality of predetermined stops defined by the adjustment collar.

15. The system of claim 14 wherein the instrument is configured to make a cut that is longer at a location proximate to the first cannula relative to the length of the cut at a location proximate to the second cannula.

16. The system of claim 14 wherein the blade is configured to angulate through the longitudinal opening.

17. The system of claim 14, wherein the shaft is longitudinally movable and lockable with respect to the adjustment collar.

18. The system of claim 17 wherein the distance is between a stop defined by the locking collar and at least one of the plurality of stops defined by the adjustment collar.

19. The instrument of claim 4, further comprising a handle connected to the shaft, wherein a portion of the handle engages, during use, a portion of the locking collar such that longitudinal movement of the shaft in a second direction is limited, and wherein the second direction is in a direction substantially opposite to the first direction.

20. The system of claim 14, wherein a portion of the adjustment collar engages, during use, a portion of the locking collar such that longitudinal movement of the shaft in a first direction is limited.

* * * * *